(12) United States Patent
Korsten et al.

(10) Patent No.: US 10,039,521 B2
(45) Date of Patent: *Aug. 7, 2018

(54) MEDICAL IMAGING SYSTEM WITH NEEDLE DETECTION CAPABILITY

(71) Applicant: KONINKLIJKE PHILIPS N.V., Eindhoven (NL)

(72) Inventors: Hendrikus Hubertus Maria Korsten, Eindhoven (NL); Peter Hendrik Nelis De With, Son en Breugel (NL); Johannes Wilhelmus Maria Bergmans, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/592,301

(22) Filed: May 11, 2017

(65) Prior Publication Data

US 2017/0238899 A1   Aug. 24, 2017

Related U.S. Application Data

(63) Continuation of application No. 14/845,397, filed on Sep. 4, 2015, now Pat. No. 9,655,588, which is a
(Continued)

(30) Foreign Application Priority Data

Mar. 3, 2010   (EP) .................................... 10155335

(51) Int. Cl.
*G06K 9/00* (2006.01)
*A61B 8/08* (2006.01)
(Continued)

(52) U.S. Cl.
CPC ............ *A61B 8/0841* (2013.01); *A61B 8/466* (2013.01); *A61B 8/483* (2013.01); *A61B 8/5207* (2013.01);
(Continued)

(58) Field of Classification Search
None
See application file for complete search history.

(56) References Cited

U.S. PATENT DOCUMENTS 6,216,029 B1   4/2001  Paltieli
8,401,250 B2   3/2013  Sangappa et al.
(Continued)

OTHER PUBLICATIONS

D. Mingyue et al, "Automatic Needle Segmentation in Three-Dimensional Ultrasound Images Using Two Orthogonal Two-Dimensional Image Projections" Medical Physics, AIP. vol. 30, No. 1 Feb. 2003 pp. 222-234.
M. Barva et al Radial Radon Transform Dedicated to Micro-Ojbect Localization From Radio Frequency Ultrasound Signal Ultrasonics Symposium vol. 3, Aug. 23, 2004, p. 1836-1839.
(Continued)

*Primary Examiner* — Tahmina Ansari

(57) ABSTRACT

A system for processing an image data volume acquired with a medical imaging acquisition device 100 from a body comprising a needle is provided. It has been realized it is advantageous to display 150 a plane intersecting the image data volume showing the needle to a user of the system. This allows better positioning of the needle. The system comprises a needle-plane determination 110 module for determining a plane being parallel to and intersecting a representation of the needle in the image data volume of the needle and being parallel to a viewing direction. The needle plane determination module may make use of pixel processing and/or spectral transformation, in particular the Gabor transform.

18 Claims, 13 Drawing Sheets

Related U.S. Application Data continuation of application No. 13/580,727, filed as application No. PCT/EP2011/052826 on Feb. 25, 2011, now Pat. No. 9,125,592.

(51) Int. Cl.
  *A61B 17/34* (2006.01)
  *A61B 8/00* (2006.01)
  *A61B 34/20* (2016.01)
  *A61B 90/00* (2016.01)

(52) U.S. Cl.
  CPC .......... *A61B 17/3403* (2013.01); *A61B 34/20* (2016.02); *A61B 2017/3413* (2013.01); *A61B 2034/2063* (2016.02); *A61B 2034/2065* (2016.02); *A61B 2090/378* (2016.02)

(56) References Cited

U.S. PATENT DOCUMENTS

| | | |
|---|---|---|
| 9,125,592 B2 | 9/2015 | Korsten et al. |
| 2003/0031368 A1 | 2/2003 | Myler et al. |
| 2007/0043458 A1 | 2/2007 | Pinnegar |
| 2007/0270687 A1 | 11/2007 | Gardi et al. |
| 2008/0221446 A1 | 9/2008 | Washburn et al. |
| 2010/0022871 A1 | 1/2010 | De Beni et al. |
| 2010/0324419 A1 | 12/2010 | Gardi et al. |
| 2011/0243431 A1 | 10/2011 | Sangappa et al. |
| 2012/0321154 A1 | 12/2012 | Korsten et al. |

OTHER PUBLICATIONS

M. Ding et al "Automatic Needle Segmentation in Three-Dimensional Ultrasound Images Using Two Orthogonal Two-Dimensional Image Projections" Medical Physics, vol. 30, No. 1, Feb. 2003 p. 222-234.

MEDICAL IMAGING SYSTEM WITH NEEDLE DETECTION CAPABILITY

FIELD OF THE INVENTION

The invention relates to a system for processing an image data volume acquired with a medical imaging acquisition device from a body comprising a needle, the system comprising a needle-plane determination module for determining a plane being parallel to and intersecting a representation in the image data volume of the needle.

The invention also relates to a medical image acquisition apparatus.

The invention also relates to a method for processing an image data volume and to a corresponding computer program product and a corresponding system.

BACKGROUND OF THE INVENTION

For some healthcare treatments, patients are injected with a needle to transfer medication or to extract or insert liquids out of and into the human body. For some treatments, the accuracy of the injection is important. If the needle is guided accurately to a specific place inside a body, e.g. a human or animal body, side-effects of the treatment are minimized. The treatment is typically performed in hospitals by a trained physician or under his supervision.

An example of a treatment where the accurate placement of a needle is a prime consideration is supplying anesthetic to a localized region of a body. The anesthetic may be needed as preparation of surgery or other treatments or care. Typical targets of the physician or the expert is to inject inside a particular local region, e.g. a particular muscle, nerve or other special element or region of the body.

If the injection needle is positioned by a medical expert, physician or the like, then the patient relies on the physician's abilities for a precise positioning of the needle in the considered region of the body.

The expert physician may analyze the local region of the body prior to the needle injection with a so-called echo-transducer device, which is based on sending ultrasound frequencies through the human skin into the body. These sound waves are reflected by the human tissue, nerves, blood vessels and the like. With a receiving device, the reflections are measured, processed and visualized on a display. After reviewing the visualizations of the local region, the physician performs the injection. Typically, however, the physician must also base his actions on his expertise and has only minor support from the echo transducer device.

SUMMARY OF THE INVENTION

Using an echo-transducer device is clearly useful in delivering local-regional medication such as anesthesia. It turns out however that using the echo-transducer device while injecting the needle is not so easy. Using an echogram a 2D picture is displayed. The thin needle and the thin ultrasound-field may result in failure to capture the needle. Only with high skill can the physician reliably find the injection needle on the displayed echo diagram. Moreover, a physician is never sure that the tip of the needle is being visualized. Part of the needle may be seen on the echogram, but the tip may be outside the ultrasound field.

It is a problem of the prior art that echo-guided loco-regional anesthesia requires high skill from the physician in operating diagnostic sonographic scanners.

The inventors have realized that part of the problem is caused by lack of a precise alignment between the thin needle and the thin ultrasound-field. Even if the physician can find part of the needle using the echo device it is not unlikely that he does not capture the full needle. The needle may be seen on the echogram, but the tip may be outside the ultrasound field. If the image data is acquired using an image acquiring head that acquires image data along a two dimensional plane, we will call that plane the acquisition plane. If the acquisition plane is visualized, but it is not parallel with the needle, maybe differing as little as a degree, then the tip of the needle may be missed on the visualization. This is very hard for the user, e.g., the physician to notice. Especially for procedures wherein precise delivery of medication is important this is important.

It would therefore be of advantage to a have an improved system for processing an image data volume acquired with a medical imaging acquisition device from a body comprising a needle. An improved system comprises a needle-plane determination module for determining a plane being parallel to and intersecting a representation in the image data volume of the needle, and a viewing direction storage for storing a predetermined viewing direction. The determined needle-plane is parallel to the viewing direction.

Using a medical imaging acquisition device an image data volume may be obtained representing the body wherein at least part of the needle has been inserted. By analyzing the image data using the needle determination device the needle may be found in the image data. For the physician this may not be enough. He (or she) should be shown a cross section which includes the full needle, so that he is sure of seeing the tip of the needle. However, simply selecting any plane coincident with the needle is confusing for the physician, who may lose his orientation. By aligning the needle plane with a viewing direction this is avoided. At any time the physician is looking at the needle from the same side and direction. For example, the viewing direction would be orthogonal to a surface of the body in which the needle is inserted and/or the viewing direction is coplanar with an acquisition plane of the acquisition device. The viewing direction may be a heart-line of an image acquisition head of the acquisition device.

A physician with the task of guiding the needle into the body further, who is shown a cross section of the image data volume which is parallel to his viewing direction but which contains a representation of the needle, is sure that he is seeing the tip of the needle. Since the needle plane is parallel to the viewing direction, the difference between this needle plane and the plane the physician is used to looking at, e.g. the acquisition plane, is minimal, thereby distorting the physician's sense of orientation to the least extend possible.

Using a high-frequency linear-array transducer with frequencies of 8-17 MHz, nerves can be visualized and surrounded by local anesthetics, using a needle. This procedure results in a higher success-rate, less local anesthetics and is considered to be safer, as it reduced the risk for intravascular injection.

Using an apparatus comprising the system it is easier for the physician to more accurately perform the needle injection. The safety of the patient is improved by reducing the chance of an injection at an incorrect location (e.g. in a vein). For the physician it is much easier to use an imaging device, such as an ultrasound system, for this purpose. The placement of the transducer on the skin above the needle is not critical anymore and the operator can concentrate completely on the image and injection itself.

It is noted that the invention can also be used with advantage with image acquisition device with measure 3d data simultaneously, instead of measuring one 2d acquisition plane at a time. Also in this case, it is useful for a physician if he sees the plane in a fixed direction, for example in the same direction in which he himself is looking at the body.

The image data volume may be a 3D data cube, e.g., represented in a computer system as a three dimensional array. Not all of the cube needs to be used. For example, the image data volume may also be represented as a data cone, possibly represented in a three dimensional array as well. Alternatively, polar coordinates may be used in the representation of data.

There are several ways to obtain the desired needle plane. Several effective ways of localizing a needle and/or a needle plane in a particular direction are disclosed in this document. It is noted that many of these methods and the devices for executing them have independent merit. In particular many of these methods can be used for localizing a needle in an image data volume without producing a needle plane in a particular viewing direction. We will discuss solutions to finding the needle and/or needle plane by processing primarily in the pixel domain and by processing in a transform domain.

For practical purposes, the plane determined to be parallel to and intersecting a representation in the image data volume of the needle may be regarded as comprising the representation in the image data volume of the needle.

In an embodiment, the medical image acquisition apparatus comprises an image data acquisition head configured for acquiring a slice of the image data volume from the body comprising the needle, the image data acquisition head being movable with respect to the body in operational use. The needle-plane determination module being configured to determine a difference in direction between the needle-plane and the image data acquisition head, e.g., a difference in direction between the needle-plane and a direction of the slice acquired by the image data acquisition head. The system being configured to indicate the difference to a user of the medical image acquisition apparatus.

As is explained further below, indicating the difference between a direction of the needle plane and the image acquisition head, i.e. a direction of the slice, allows a user of the system to reposition the image acquisition head so that the slice of the image data volume that it acquires coincides with the needle plane. After the re-positioning the user has a better view of the needle since it is better contained in the plane which the image acquisition head is acquiring. In particular, the risk is reduced that the tip of the needle is not seen, i.e. acquired, by image acquisition head.

In an embodiment, the needle-plane determination module comprises a data projection module for projecting the image data volume in a projecting direction onto a projection plane, and a projected needle-line determination module for determining a projected needle-line being comprised in the projection plane, the projected needle-line being parallel to and intersecting a projected representation of the needle in the projection plane.

By projecting the image data volume, the problem of finding a needle in a three dimensional data volume is reduced to finding a needle in a two dimensional data volume. This simplifies the problem considerably. It is noted that the plane defined by the projected needle and the projecting direction comprises the representation of the needle itself in the image data volume.

It is generally noted that since the needle is thin it can for practical purposes be regarded as a line. Even if the thickness of the needle were to play a role, the needle may be approximated with its heart line, going through the tip of the needle. If the needle shows up in image data as thicker than a line, it can be approximated as a midline.

A line which is parallel to and intersects another line can for practical purposes be regarded as collinear with the other line. Advantageously, the projected needle-line is collinear with or comprises the projected representation of the needle in the projection plane.

In an embodiment, the data projection module is configured for integrating the data volume along the projecting direction.

The intensity of the needle in the captured image data is found to be higher from the intensity of the body itself. In particular for images obtained from sonographic scanners, e.g., ultrasound acquisition device producing an echogram, the needle has been found to produce a higher intensity. By summing the data along the projecting directing this effect is amplified. As a result, the position of the needle is found by capturing the needle as a straight white line in the projected image. In other words, a two dimensional data histogram is produced from the three dimensional data set.

This can be improved by only considering voxels with an intensity above a predetermined threshold. A voxel (volumetric pixel) is a volume element, representing a value on a regular grid in three dimensional space. This reduces the influence of measurement coming from the body relative to measurements coming from the needle. As a result the, needle shows up even better in the projected 2d data set. Automated detection of the needle can be based on the histogram-forming technique in which the intensities, or similar image-forming signal components, are integrated, e.g. summed within the 3d data set. For example, the intensities may be projected towards the surfaces of a 3D data cube. For each (or some) particular point in the projection plane the intensities are summed along the line going through the particular point and parallel to the projection direction.

Projecting the data is an example of pixel-based processing.

In an embodiment, the projecting direction is perpendicular to the projection plane.

In an embodiment, the projecting direction is parallel to the viewing direction. The needle-plane detector is configured to determine the plane parallel to the viewing direction and comprising the projected needle-line. By projecting parallel to the viewing direction the needle plane can be found efficiently. In the projection plane the projected needle is found.

For example, using the integrating technique mentioned above, the needle will stand out. Not that it is sufficient to merely determine a projected needle line, i.e., a line lying in the projection plane coinciding with the needle. The plane defined by the projection direction and the projected needle-line is in this case also parallel to the viewing direction.

We will refer to a projection plane, orthogonal to the viewing direction, as the ground plane.

Note that it is not necessary that the projection plane is orthogonal to the projection direction. This fact may be used for optimizing the representation of the projected needle in the projection plane. There is a trade-off involved here, as the projection plane is more orthogonal the needle, the intensity of the projected needle increases. On the other hand, if the projection plane is parallel to the needle, the projected needle is longer, thus the projected needle line can be determined more accurately.

The projection plane may also be chosen orthogonal to the viewing direction. This simplifies the implementation and reduces artifacts based on the fact that the image data need not be of the same thickness along all possible projection planes.

The projection embodiment described above have the advantage that it is not necessary to localize the precise three dimensional location of the needle. Instead it is sufficient to find a line comprising a projection of the needle. Any plane going through the projected needle line and the projection direction also contains the needle. Having a needle plane is sufficient for visualization software to show an image of the needle. The physician can see himself where the needle is, and in particular where the tip of the needle is.

In an embodiment, the needle-plane determination module comprises a needle-line determination module for determining a needle-line being parallel to and intersecting the representation in the image data volume of the needle. The needle-plane detector is configured to determine the plane parallel to the viewing direction and comprising the needle-line.

It is also possible to determine the three dimensional location of the needle more exactly. From this information the needle plane can be calculated in a straightforward manner. Note that, also in this embodiment it is not necessary to find the needle more precisely than the needle line, e.g., the tip of the needle need not be explicitly located. Having this more precise location of the needle is of course not an impediment to using this method of finding the needle plane. Note that any known needle detection algorithm can be used to determine the needle line. The needle plane can be determined from the needle line as the plane comprising the needle line and parallel to the viewing direction.

In an embodiment, the needle-plane determination module comprises a data projection module for projecting the image data volume onto at least a first projection plane and onto a second projection plane, and a line detection module for detecting a projected representation of the needle in the projection plane.

By projecting the image data volume onto a projection plane, detecting the projected needle in the plane a plane can be constructed parallel to the projection direction and comprising the projected needle. By doing this twice the needle-line can be found as the intersection of the twee needle planes. It may be advantageous to project multiple times to find two directions in which the needle can be detected well. Note that the first and second projection plane may be orthogonal, but this is not necessary.

An advantage of determining a needle plane directly from the data or via the intermediate step of determining a needle line, avoids determining the tip of the needle. Finding the precise location of the tip is relatively hard for image analysis but relative easy for a physician provided he tracking the needle on a screen with an acquisition plane that is aligned with the needle plane.

In an embodiment, the needle-plane determination module comprises a spectral transformer for transforming at least part of the image data volume into a transformation domain using a directionally sensitive spectral transformation.

Apart of determining the needle plane from processing on the pixels themselves, the processing may also involve processing in a transformed domain.

The inventors had the insight that a transform can be chosen which explicitly aims at describing the properties of the needle. The key properties of the needle are: it is a line segment with a certain orientation. When considering this, two transforms may be used to emphasize those features: a transform that searches for line structures, e.g. the Hough transform, and a directionally-sensitive transform, such as the Gabor or rotational wavelet transform.

We have evaluated the Hough and Gabor transform for this purpose, and it showed that the last is superior to the first in detecting the needle. Although, transforming the data slices taken from the 3D data set could be done with a signal transform that is particularly sensitive to the occurrence of line segments, for example, the Hough transform is sensitive to line segment, it has been found though that this approach has its problems. In particular, the Hough transform will react to any line like material in the image data. When multiple candidates for the line are found the Hough transform gives no good way to select among the multiple possibilities. Instead a better approach is to use a directionally sensitive transformation.

In an embodiment, the directionally sensitive spectral transformation is a Gabor transform or a rotational wavelet transform. With the Gabor transform, it is possible to determine the sinusoidal frequency and phase content of a specific part of an image. This can be used to detect the needle.

In an embodiment, the system for processing an image data volume comprises a data projection module for projecting the image data volume in a projecting direction onto a projection plane, and wherein the spectral transformation is applied to the projection plane.

Using a transform is particularly effective in two dimensions, as advantage can be taken of the increased intensity of the projected needle in the projection plane relative to the other measurements.

In an embodiment, the needle-plane determination module comprises an ellipsoid detector for detecting an ellipsoid in the transformation domain, and a primary axis determination module for determining a primary axis of a detected ellipsoid.

After transformation of the image data using a directionally sensitive transform, the needle tends to shows up as an ellipsoid. By detecting the ellipsoid and determining its primary axis the orientation of the needle is determined. An orientation in a plane, e.g. of a projected needle, may for example be expressed as an angle that a line through the projected needle makes with a fixed predetermined line, say an axis.

In an embodiment, the needle-plane determination module is adapted to transform the at least part of the image data volume into a transformation domain at least twice wherein the directionally sensitive spectral transformation is configured for different directions, and wherein the ellipsoid detector is configured for selecting a direction from the different directions having an ellipsoid in the transformation domain corresponding to the selected direction having a best fit to the needle.

A directionally sensitive transform such as the Gabor transform is typically configured to be sensitive to one particular direction. By performing the transform for multiple directions a direction can be found in which best shows a particular direction. Since the needle responds very well to a directional transform, provided the direction in which the transform is sensitive corresponds with the direction of the needle, this direction is presumably the direction of the needle.

In an embodiment, the needle-plane detector is configured to determine the needle-plane in dependence upon the orientation of the primary axis.

Once the direction of the needle is known it can be found in the projected image easily. For example, a (virtual)

sample needle in the found direction can be correlated with the projected image data at all possible locations. The location where the correlation is highest corresponds to the projection of the real needle.

In an embodiment, the system for processing an image data volume comprises a display module for displaying a representation of the image data in the intersection between the needle plane and the image data volume.

By showing the intersection of the needle plane to a physician he has a better understanding of where his needle tip is in relation to the anatomy which may also be seen on the visualization of the intersection. Moreover, if the needle plane is parallel to the physicians viewing directions, as can be configured in the viewing direction storage, the risk of disorientation on the side of the physician is minimized.

A further aspect of the invention concerns a medical image acquisition apparatus comprising the system. The visualization is particularly useful if it is shown to the physician during the performance of the procedure. It is noted however that the system can also be employed in a medical image workstation, for processing of image data acquired earlier. For example, to review an operation done earlier, the method may be employed.

In an embodiment of the medical image acquisition apparatus, the apparatus comprises an image data acquisition head configured for acquiring a slice of the image data volume from a body comprising the needle. The image data acquisition head can be rotated around an axis, the axis being parallel to the viewing direction in operational use. The needle-plane determination module is configured to determine a difference in direction between the needle-plane and the image data acquisition head. The medical image acquisition apparatus is configured to indicate the difference to a user of the medical image acquisition apparatus.

For tracking the needle as it is being inserted into the body, while using a head which acquires image data along a two dimensional acquisition plane, it is best if the needle is lying in the acquisition plane. As noted above however, it is not so easy to align the acquisition plane with the needle. By acquiring a volume of image data, the apparatus can determine the position of the needle with respect to the head. In particular, a difference in orientation between the needle plane and the acquisition plane can be determined. For example, the difference in orientation may be expressed as the angle in degrees. For example, the needle plane and the acquisition plane intersect a projection plane, say the ground plane, in two lines, the angle these two lines make can be expressed as an angle in say degrees and shown to the user. By reporting a similar angle with respect to a different projection plane, say the plane parallel to the viewing direction but orthogonal with the needle plane, a second orientation difference can be detected and reported to the user. In this way the user can be guided to align his image acquisition head with the needle plane in a particularly effective manner.

A further aspect of the invention concerns a method for processing an image data volume acquired from a body comprising a needle with a medical imaging acquisition device. The method comprises storing a predetermined viewing direction, determining a needle-plane being a plane parallel to and intersecting a representation in the image data volume of the needle. The needle-plane is parallel to the viewing direction.

A method according to the invention may be implemented on a computer as a computer implemented method, or in dedicated hardware, or in a combination of both. Executable code for a method according to the invention may be stored on a computer program product. Examples of computer program products include memory devices, optical storage devices, integrated circuits, servers, online software, etc.

In a preferred embodiment, the computer program comprises computer program code means adapted to perform all the steps of a method according to the invention when the computer program is run on a computer. Preferably, the computer program is embodied on a computer readable medium.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the system, can be carried out by a person skilled in the art on the basis of the present description.

A person skilled in the art will appreciate that the method may be applied to multidimensional image data, e.g., to 2-dimensional (2-D), 3-dimensional (3-D) or 4-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

A system for processing an image data volume acquired with a medical imaging acquisition device from a body comprising a needle is provided. It has been realized it is advantageous to display a plane intersecting the image data volume showing the needle to a user of the system. This allows better positioning of the needle. The system comprises a needle-plane determination module for determining a plane being parallel to and intersecting a representation in the image data volume of the needle and being parallel to a viewing direction. The needle plane determination module may make use of pixel processing and/or spectral transformation, in particular the Gabor transform.

In an improved system for processing an image data volume acquired with a medical imaging acquisition device from a body comprising a needle, the system comprises a viewing direction storage for storing a predetermined viewing direction, and a needle-plane determination module for determining a plane parallel to the viewing direction and parallel to and intersecting a representation in the image data volume of the needle. The needle-plane determination module determined the plane, i.e. the needle plane, in dependency upon the viewing direction.

BRIEF DESCRIPTION OF THE DRAWINGS

The invention is explained in further detail by way of example and with reference to the accompanying drawings, wherein:

FIG. 9 (bottom) shows a schematic representation of the projection of the image volume onto the ground plane.

Throughout the Figures, similar or corresponding features are indicated by same reference numerals.

LIST OF REFERENCE NUMERALS

Figure 1:
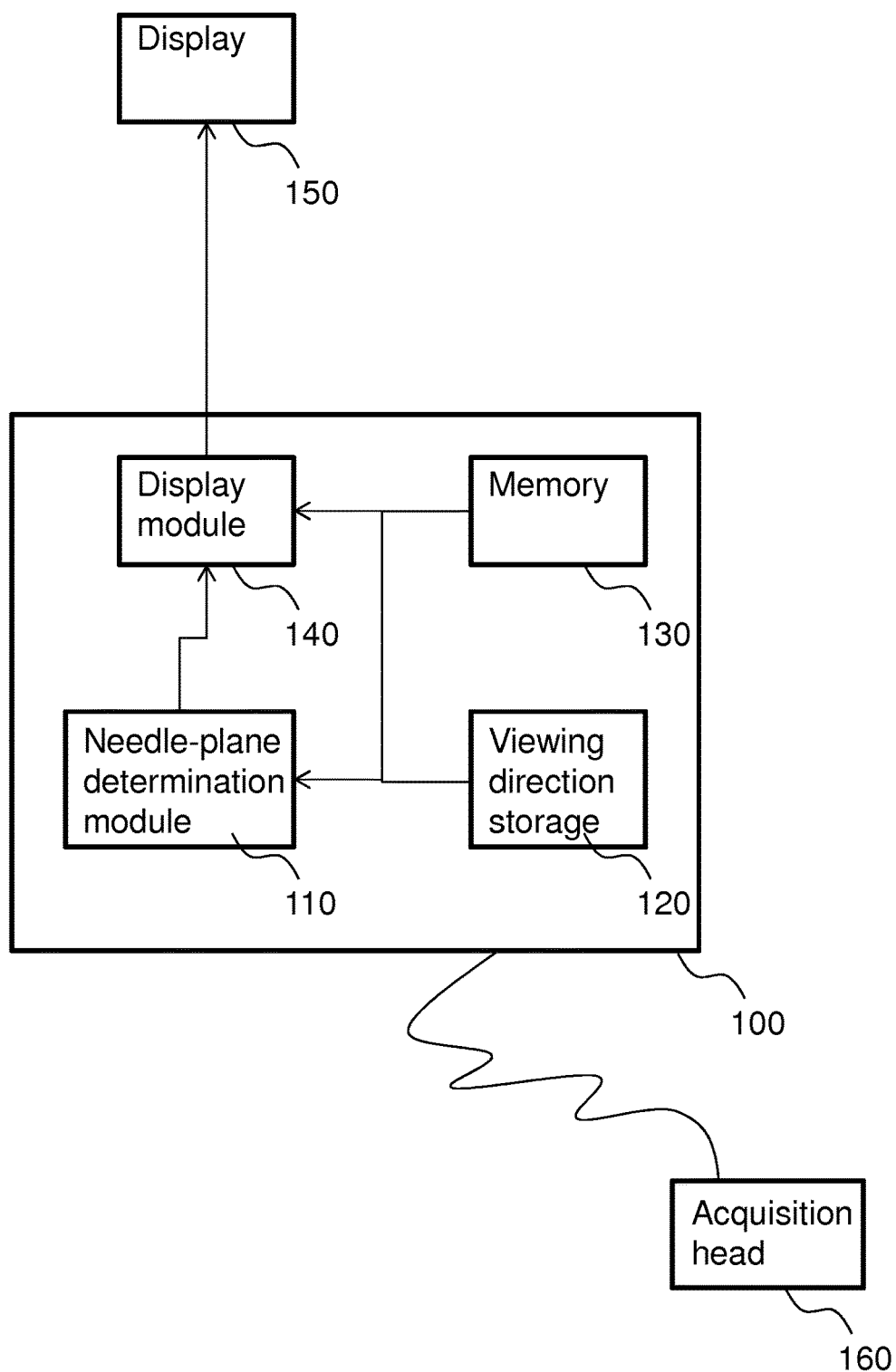
FIG. 1 is a block diagram illustrating an embodiment of a medical acquisition device according to the invention.

100 a medical image acquisition apparatus
110 a needle-plane determination module
120 a viewing direction storage
130 a memory
140 a display module
150 a display
160 an image data acquisition head
210 a data projection module
220 a projected needle-line determination module
230 a needle-line determination module
240 a spectral transformer
310 an ellipsoid detector
320 a primary axis determination module
410 a needle visualization method
420 obtaining three dimensional image data volume
425 determining a needle plane
430 visualizing the needle
440 a needle visualization method
450 projecting the image data volume onto a projection plane
452 transforming the projected image data volume with a Gabor transform configured for a particular direction
454 determining the fit of the particular direction
456 iterating the transforming for a different particular direction
458 locating the projected needle
460 determining the needle plane
500 a needle visualization system
510 a medical image acquisition apparatus
520 a medical image acquisition head
530 a medical image workstation
540 a needle
542 tissue
544 a field of view
550 a reconstructed image
600 an echogram
610 a representation of a needle
620 needle reflections
1210 a needle plane
1220 an acquisition plane
1215, an angle between a needle plane and an acquisition plane
1225

Detailed Embodiments

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described.

FIG. 1 shows a medical image acquisition apparatus 100. Some of the possible data dependencies between the different elements of medical image acquisition apparatus 100 are indicated in the figure with arrows.

Medical image acquisition apparatus 100 is connected, or connectable, to an image data acquisition head 160. Medical image acquisition apparatus 100 and image data acquisition head 160 together allow for the acquisition of medical image data from a body, such as a human or animal body. For example, medical image acquisition apparatus 100 may be an ultrasound apparatus and image data acquisition head 160 may be configured to send the appropriate sound waves and receive their reflections.

Image data acquisition head 160 may be a configured for receiving image data in three dimensions; in that case the image data volume can be obtained from the acquiring apparatus directly. Image data acquisition head 160 may also be an acquisition device that obtains image data along a two dimensional acquisition plane. In that case a preprocessing step may be needed to obtain the image data volume. For example, the operator of medical image acquisition apparatus 100, e.g., the physician, may sweep image data acquisition head 160 over the surface of the body. In this way multiple images are acquired along multiple acquisition planes. Preferably, the multiple acquisition planes are parallel or approximately so. Preferably, the needle is kept stationary during the sweep. This way of acquiring images is best suited if the body moves relatively little, for example, for injection in regions away from the heart. Medical image acquisition apparatus 100 may contain an image volume preprocessor (not shown) for combining multiple two dimensional images obtained from multiple acquisition planes into a single three dimensional data volume. In general, known techniques for combining two dimensional slices into a three dimensional image volume, in particular as related to ultrasound images, can be used with the invention.

Image data acquisition head 160 may comprise an ultrasound transmitter. The ultrasound transmitter may be configured for emitting a beam with a circular opening angle of, say, 60-90 degrees. The reflections measured in image data acquisition head 160, result in an insight of a rectangular slice of the body of a certain depth. The length of the slice is determined by the aforementioned spreading angle of the emitter. By slowly moving the device over the patient's body, the physician obtains a view of the local region of the body, and sees basically a series of slices.

Medical image acquisition apparatus 100 comprises a memory 130 for storing the image data volume. Memory 130 may also be used as temporary processing memory. Medical image acquisition apparatus 100 comprises a viewing direction storage 120. Viewing direction storage 120 may be comprised in memory 130. The viewing direction can be stored in the form of a vector. The viewing direction may also be implicit. For example, medical image acquisition apparatus 100 may be configured that the viewing direction is assumed to be the heart line of image data acquisition head 160, e.g. a centerline of the acquisition plane.

Medical image acquisition apparatus 100 comprises a needle-plane determination module for determining the needle plane. The needle plane is a plane intersecting the image data volume, intersecting the representation of the needle in the image data volume, and running parallel to the viewing direction. Different embodiments of needle-plane determination module 110 are disclosed below. Needle-plane determination module 110 is connected to memory 130 for access to the image data volume. Needle-plane determination module 110 is connected to viewing direction storage 120 for access to the viewing direction.

Medical image acquisition apparatus 100 comprises a display module 140 and a display 150. Display module 140 is configured for selecting and processing the image data volume for displaying on display 150. Display module 140 is connected to memory 130 for access to the image data, and to needle-plane determination module 110 for access to the determined needle-plane. Display module 140 may also have access to the viewing direction. For example, given the image data and the needle-plane, display module 140 may compute a representation of the intersection of the image data volume and the needle plane and show it on display 150. It is possible the needle plane does not coincide exactly with the current acquisition plane of image data acquisition head 160. In that case display module 140 may show two images, one of the current acquired images and one from a computed intersection.

Figure 2:
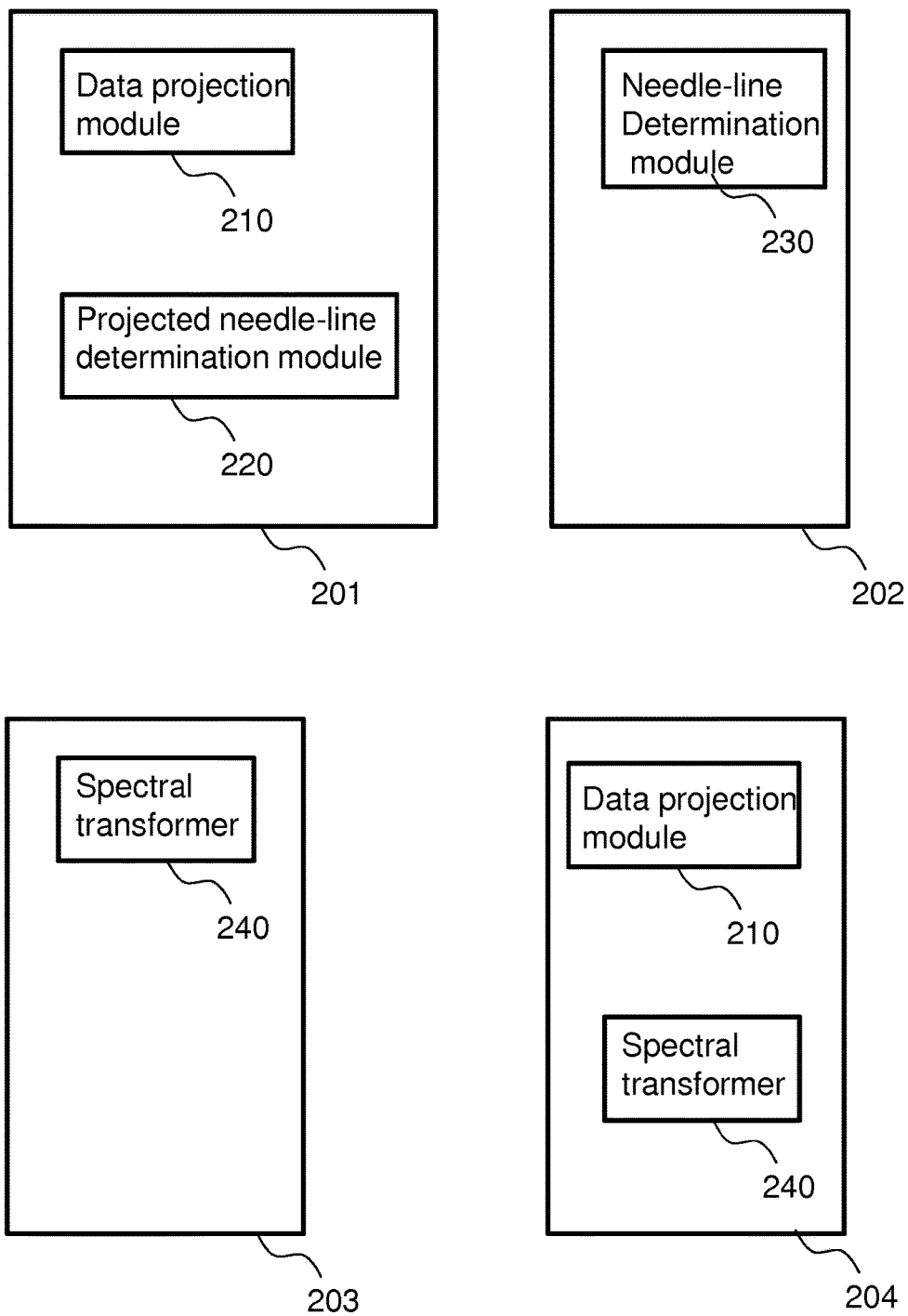
FIG. 2 is a block diagram illustrating four embodiments of a needle-plane determination module.
Figure 3:
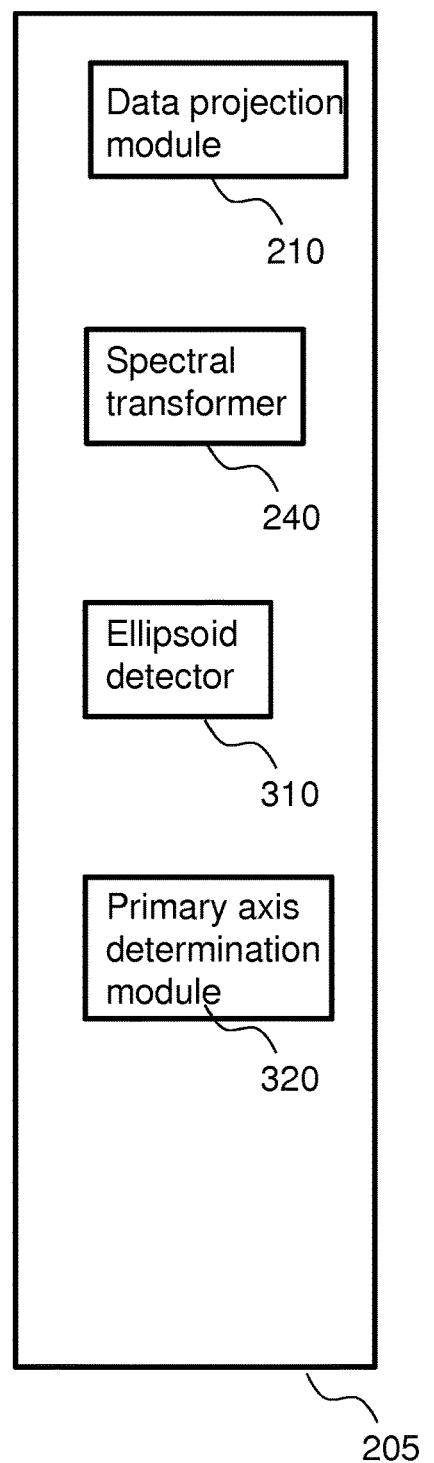
FIG. 3 is a block diagram illustrating a fifth embodiment of a needle-plane determination module.

FIGS. 2 and 3, showing embodiments of needle plane determination modules, are discussed further below.

Figure 4A:
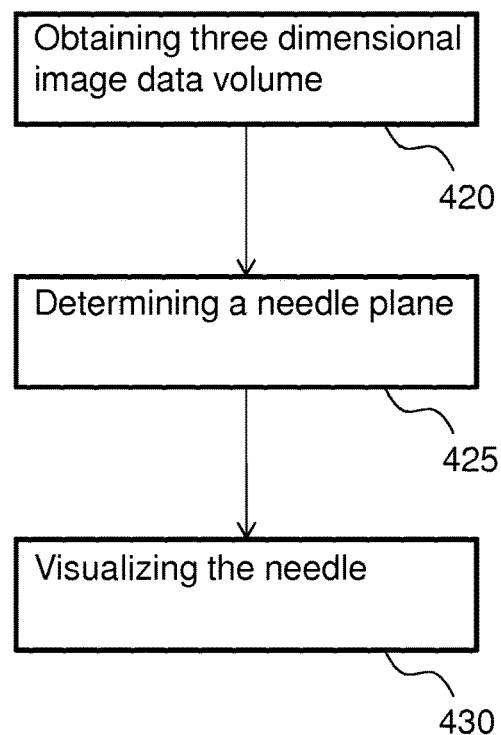
FIGS. 4a and 4b illustrates a needle visualization method according to the invention in the form of a flow chart.
Figure 4B:
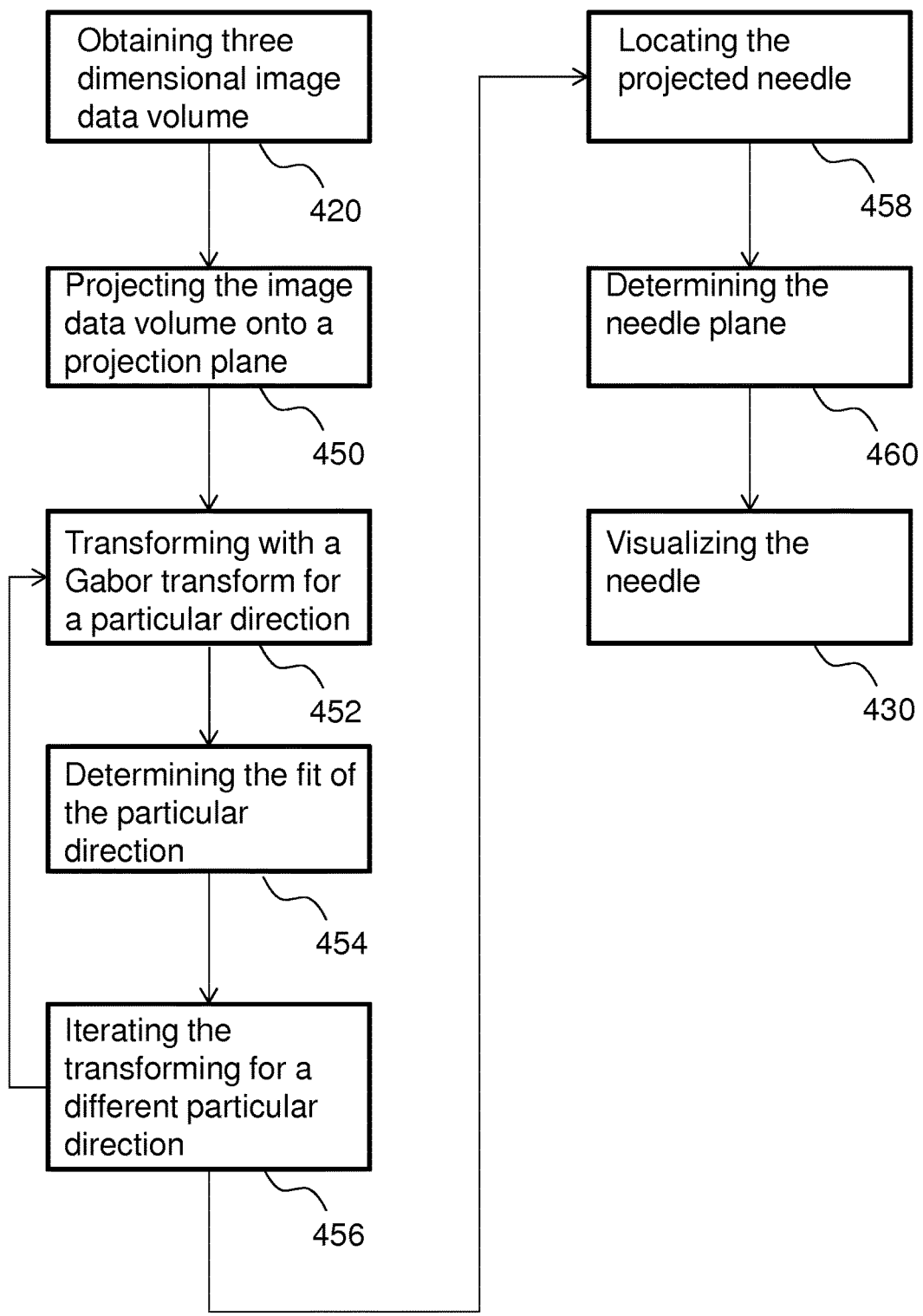

FIG. 4a shows a flows chart that illustrates a method for needle visualization 410 according to the invention. FIG. 4b is a more detailed embodiment which is described further below.

In step 420 three dimensional image data volume is captured. The image data volume may be obtained using a device that acquires in three dimensions. The image data volume may also be obtained by combining multiple two dimensional images. In step 425 needle plane is determined. There are various ways to obtain the needle plane. For example, the needle plane can be obtained directly from the image data, using only pixel based processing or using also spectral transforms. The needle plane can be obtained by first determining a needle line, possibly from a tip and starting point of the needle. From a needle line, a needle plane can be determined. In step 430 the needle is visualized. For example, an intersection is shown of the image data volume with the needle plane. The needle may also be shown in other ways, for example, the needle or needle-line can be shown in a three dimensional rendering of the image data volume.

Figure 5:
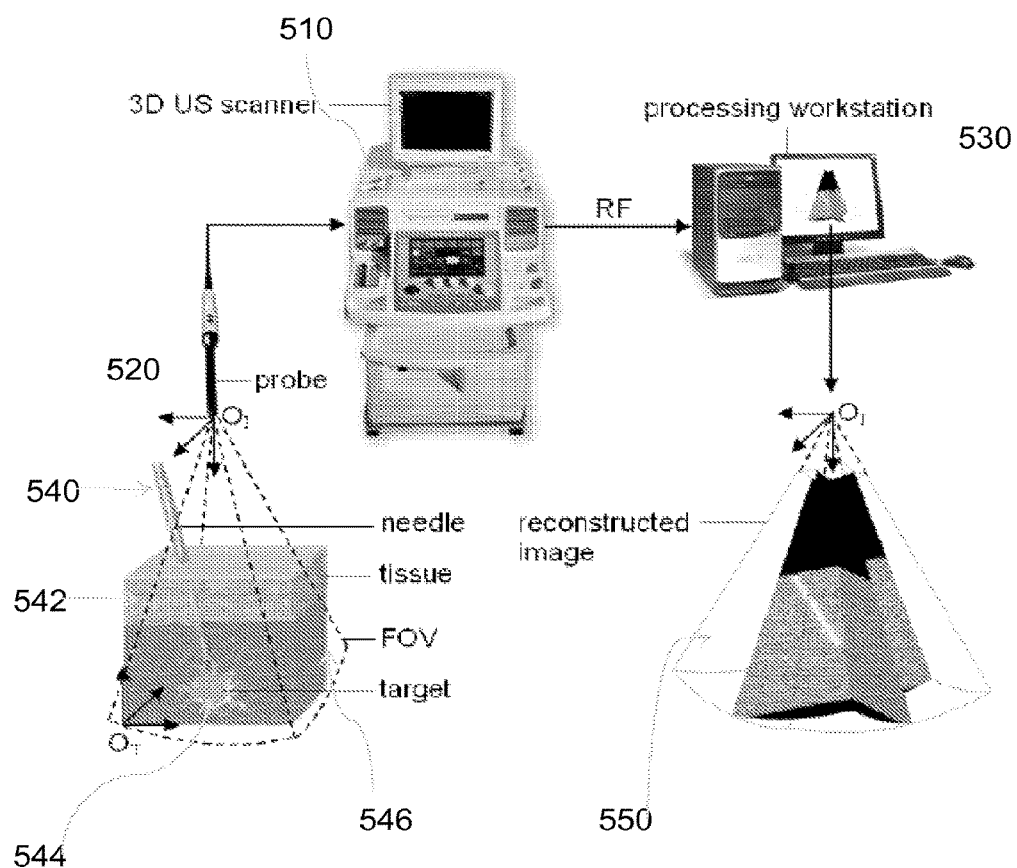
FIG. 5 illustrates a medical acquisition device and workstation according to the invention.

FIG. 5 shows how a set-up that may be used for needle visualization and in particular to perform the method shown in FIGS. 4a and/or 4b.

The image data volume may be obtained by a medical image acquisition head 520 (also referred to as a probe) connected to a medical image acquisition apparatus 510. FIG. 5 shows a probe which is capable of obtaining three dimensional measurements. The probe is acquiring images from a tissue 542 in which a needle 540 has been partly inserted.

Figure 10A:
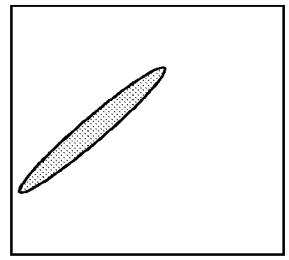
FIG. 10*a* illustrates a transformed domain using the Gabor transform
Figure 10B:
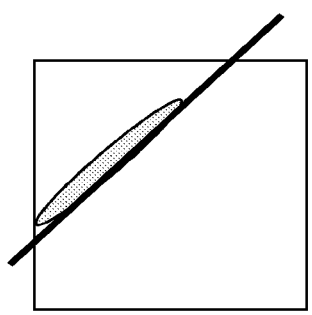
FIG. 10*b* illustrates a primary axis.
Figure 10C:
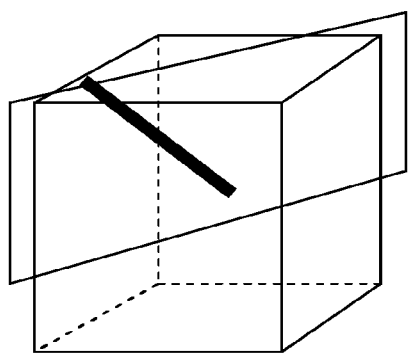
FIG. 10*c* illustrates a needle plane.

Medical image acquisition head 520 has a limited field of view 544. Probe 520 is connected to medical image acquisition apparatus 510. The image data volume can be processed on medical image acquisition apparatus 510 or on a processing workstation 530. A display shows the reconstructed image 550 including a representation of the needle. Note that the needle plane is not shown in FIG. 5. A schematic indication of the needle plane is shown in FIG. 10c (discussed below).

If needle 540 is redirected, a new needle plane can be recalculated almost immediately and displayed. This option is especially useful if a three dimensional acquiring probe is used.

Figure 6:
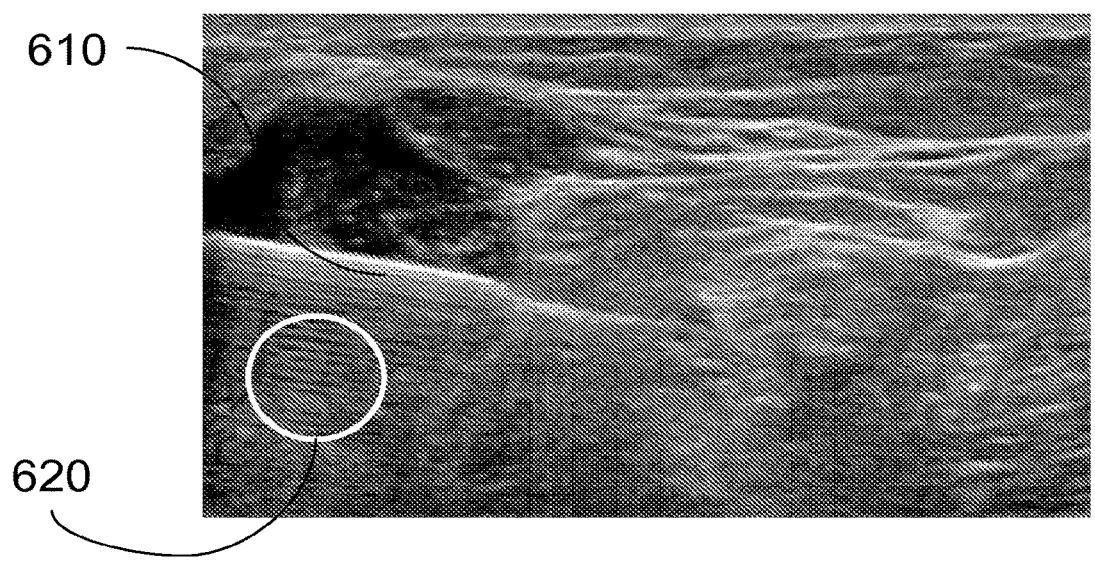
FIG. 6 shows an echogram of a body comprising a needle.

FIG. 6 shows an echogram obtain from a tissue with a needle such a tissue 542. Clearly visible is a needle 610. As can be seen in FIG. 6 it is not clear if the tip of the needle is included in the echogram, and if so where exactly it is located. Presumable, the acquisition plane was not perfectly aligned with the needle plane. From a collection of images such as shown in FIG. 6 the image volume can be reconstructed. From the constructed image volume a constructed echogram like picture can be computed showing the full needle, having the same viewing direction as FIG. 6. Even if the acquisition plane is not perfectly positioned, the user the system can obtain the correct intersection, showing the needle along its full length, in particular showing the tip of the needle. FIG. 6 also shows needle reflections 620. The needle reflections are artifacts caused by the used ultrasound technique. It is presumed that the needle reflections are related to the thinness of the needle. As will be further discussed below, the reflections may be a hindrance in determining the location of the needle and/or needle plane.

Figure 11:
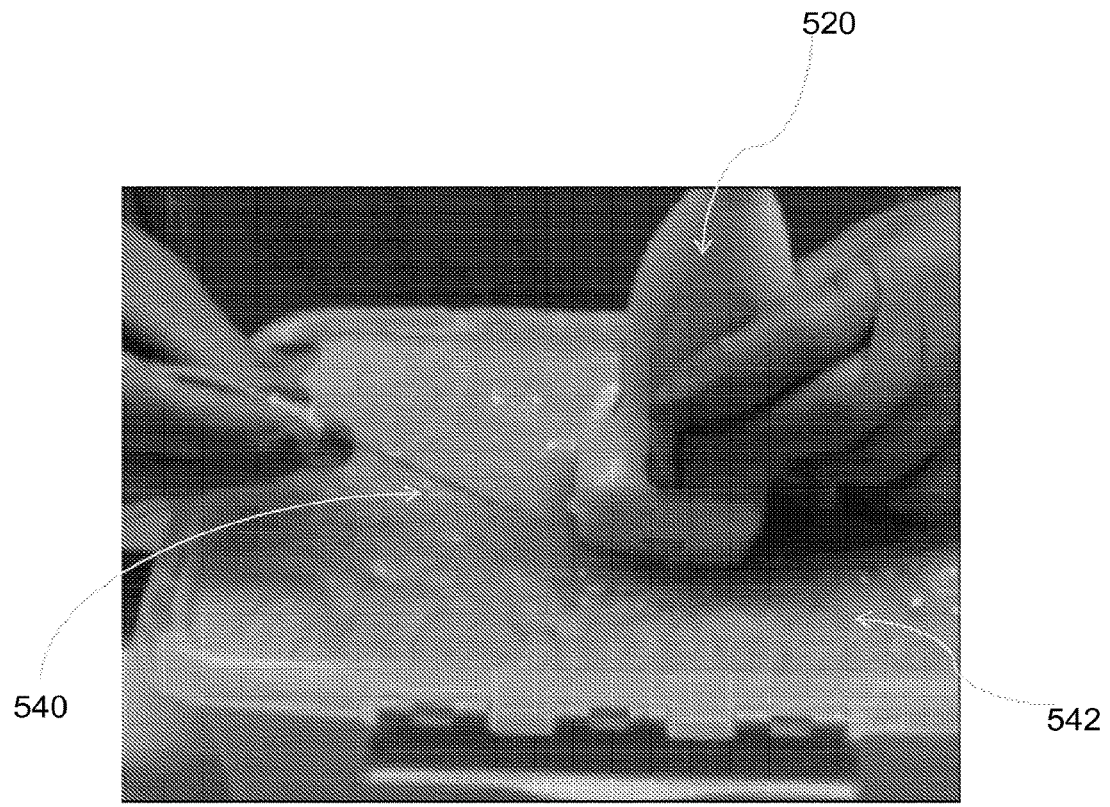
FIG. 11 shows a physician inserting a needle using an image data acquisition head.

FIG. 11 shows a physician performing the procedure on an agar phantom. Shown is a physician inserting a needle 540 into tissue 542 with one hand, while the other holds a medical image acquisition head 520 to guide his actions. FIG. 11 will be discussed more fully below.

FIG. 2 shows embodiments 201, 202, 203 and 204 of needle-plane determination module 110. FIG. 3 shows embodiment 205.

Needle-plane determination module 202 comprises a needle-line determination module 230. In general any needle-line determination method can be used to obtain the needle plane. Below we describe one particular way of obtaining the needle-line using projection.

For this purpose needle-plane determination module 202 may comprise data projection module 210 and a projected needle tip determination module (not shown).

Figure 7:
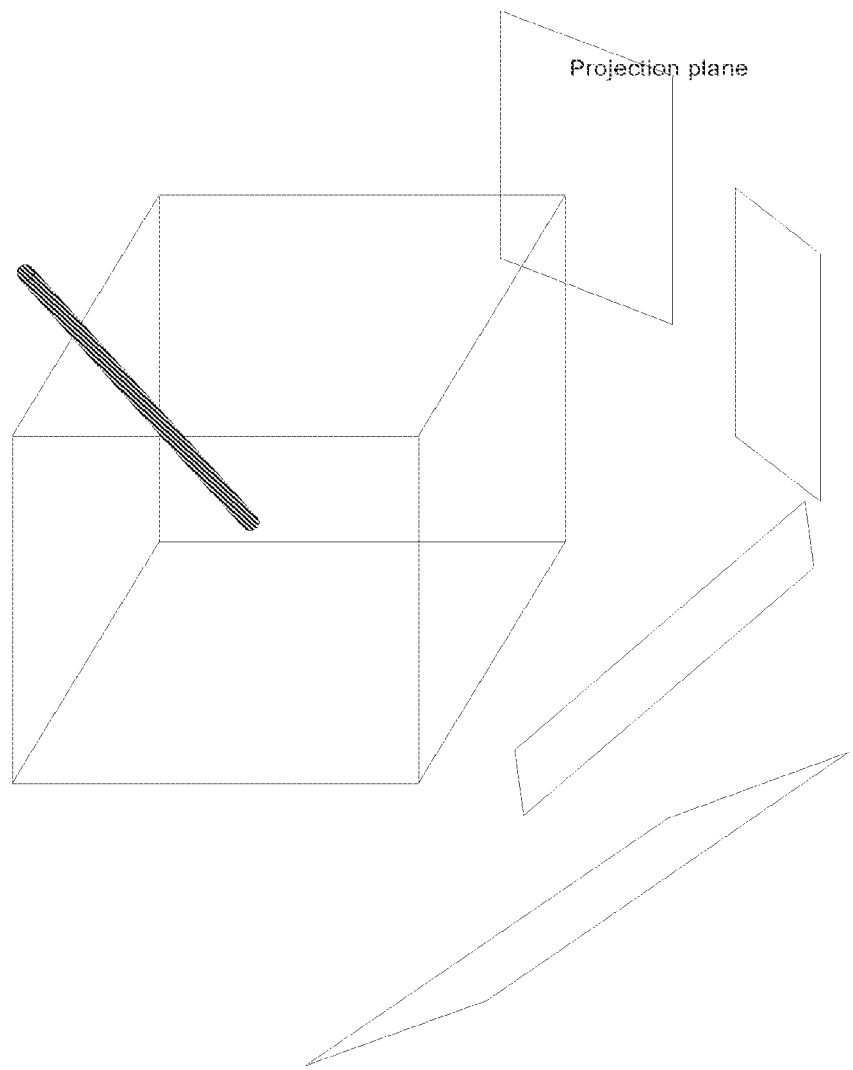
FIG. 7 illustrates a data cube with needle and various projection surfaces.

For the localization of the needle line (also referred to as needle axis) in a 3D image data one can use parallel projection. A projection transformation of the 3D dataset onto a given set of projection planes with different orientations can be applied. FIG. 7 shows this in schematic form. A data cube having a needle inside is projected on several projection planes (four projection planes are shown). If the needle is perpendicular to the projection planes, it will show up as a high intensity peak on the projection plane. The needle tip is found by taken an optimal threshold that exploits prior probability densities of the needle and background voxel intensities. For example, a pixel intensity can be predetermined, a pixel on a projection plane with an intensity above the predetermined pixel intensity is assumed to correspond to the needle plane tip. Once the needle tip is found, the needle line can be easily determined. It is the line which is parallel to the projection direction which passes through the found projected needle tip.

This can be formalized as follows:

To determine the position of the needle in 3D US data, the parallel projection can be used. By applying the parallel projection transformation on a 3D dataset for a given set of projection planes with different orientations we map an image as a function $I(x, y)$ representing volume data to plane function $P(u, v, \alpha, \beta)$. Parameter $P(u, v, \alpha, \beta)$ describes its projections as a function of the 2-D displacement $(u, v)$ and the projection direction determined by two angles (α, β), formally expressed as $$P(x,y,\alpha,\beta)=\Sigma I(R(\alpha,\beta)*(u,v)),$$

where $R(\alpha, \beta)$ is the projection matrix which is depending on the direction of normal vector of projection plane. The normal vector of the plane is rotated around the x-axis by angle a, and around the y-axis by angle β.

$$\vec{n} = \langle 1, 0, 0\rangle$$

$$S(\alpha) = \vec{n}\begin{bmatrix} \cos(\alpha) & \sin(\alpha) & 0 \\ -\sin(\alpha) & \cos(\alpha) & 0 \\ 0 & 0 & 1 \end{bmatrix}$$

$$R(\alpha, \beta) = S(\alpha)\begin{bmatrix} \cos(\beta) & 0 & \sin(\beta) \\ 0 & 1 & 0 \\ -\sin(\beta) & 0 & \cos(\beta) \end{bmatrix}$$

By summation of all voxel intensities in the same directions as the normal vector of the projection plane, we project the 3D volume to the 2D surface. The result will be a high peak on one of the projection planes if the needle is parallel to that normal vector of the plane. Once a projection plane is found in which the needle shows up as single point, the needle line can be obtained as the line which is incident with the projected tip and parallel to the projection direction.

To compute the maximum parallel projection transformation we discrete the orientation of our projection planes by the discretization steps Δα and Δβ. Δα and Δβ must be sufficiently fine to avoid missing the needle.

Needle-plane determination module 201 comprises a data projection module 210 and a projected needle-line determination module 220.

It is not always required that the needle itself is detected but only the vertical plane through it. It is possible to detect the two-dimensional plane directly from the 3D dataset, instead of detecting the one-dimensional needle and then taking the vertical plane through it. Below one way of accomplishing this is described. Data projection module 210 projects the image data volume onto a projection plane. We will use the ground plane in this example embodiment. The ground plane is orthogonal to the viewing direction. We will also assume that the projection direction and the viewing direction are parallel, although this is not necessary.

The dataset d(x, y, z) is reduced to two dimensions:

$$d'(x, y) = \sum_z d(x, y, z)$$

for all (x, y). Note that in this representation the z-axis corresponds with the projection direction. By summing all values with identical x and y values, all data points corresponding to one vertical line are summed. The summation preserves needle information but suppress noise as much as possible. In a refinement of this embodiment, a filter can be used in a direction aligned with the needle's orientation. The noise can further suppressed by applying a threshold to the data before summating. For example, all data values below a noise threshold are ignored for the summation. A resulting two dimensional dataset d'(x, y) contains the information needed to detect the vertical plane in which the needle is positioned. The only information that is lost is the location of the needle inside this vertical plane.

Figure 9:
FIG. 9 (top) shows a projection of an image volume onto a ground plane.
Figure 9:
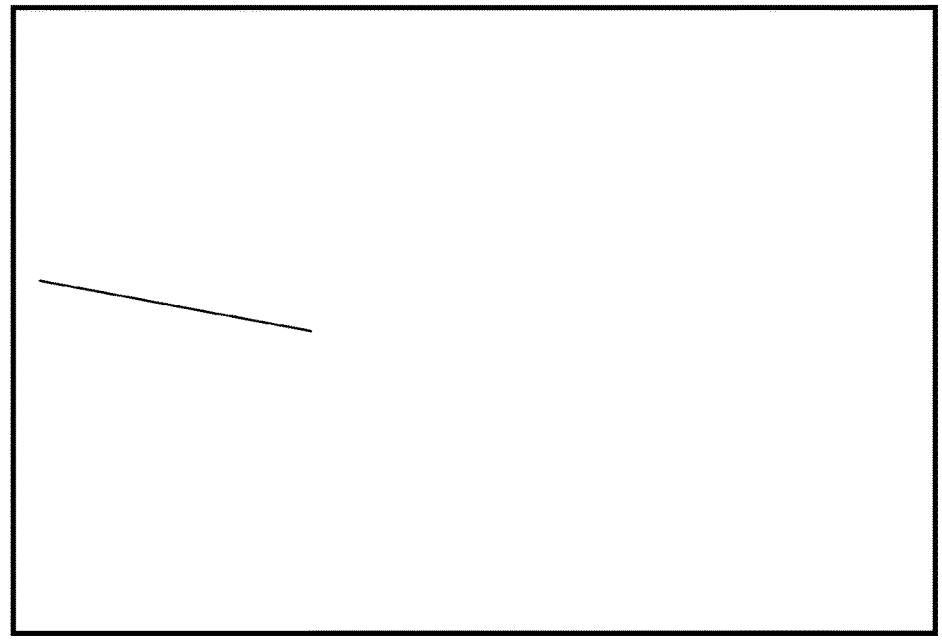

This method was tested on a real datasets. The resulting dataset is shown in FIG. 9 (top). The needle information is clearly visible as desired. The needle position is schematically illustrated in FIG. 9 (bottom). This two-dimensional dataset can now be used to feed a fast two-dimensional line detector, e.g., a Hough transform. The needle plane can be determined as the vertical plane going through the detected projected needle, that is, the plane through the detected projected needle parallel to the viewing direction.

This algorithm works best if the brightness of the needle is high compared with the brightness of the tissue. That is if the needle is of such material that is reflects ultrasound well and/or is not too thin. The difference in brightness in the datasets can also be caused by the dependency of the needle's brightness on the direction in which the scans are taken. If the contrast between the projected needle and the surrounding tissue is sufficient a line detector will work. However, if the contrast is lower a line detector may not be sensitive enough, even though enough information regarding the needle is present in the projected image. In that case a directionally sensitive transform produces better result. Even though a full line may not be sufficiently visible enough of the direction may is typically still present.

Needle-plane determination module 203 comprises a spectral transformer 240. Using a spectral transform is advantageous since it can be arranged to be sensitive to a particular direction. As a result the transformation is less sensitive to noise which is typically less directional.

Moreover, a directional transform has the advantage that it is not, or significantly less, disturbed by needle reflections which may be present in the echogram. See, for example, FIG. 6, the reflections indicated at 620. The reflections generally run in the same direction as the needle and do not influence a correct determination of the needle direction. A second phase, determining the needle location and/or needle plane from the found needle orientation, is also less influenced by the reflections since the real needle will generally give a better fit than its reflections.

Before applying spectral transformation the data set may be reduced to a two dimensional data set, as is illustrated in FIG. 9. This method may be employed by needle-plane determination module 204 which comprises a data projection module 210 and a spectral transformer 240.

We will discuss a transformation based detection method using needle-plane determination module 205 comprises a data projection module 210 and a spectral transformer 240, an ellipsoid detector 310 and a primary axis determination module 320.

The Gabor transform is a special case of the short-time Fourier transform. First, the image is multiplied by a Gaussian function to give more weight to the area of interest. Then, the Fourier transform is used to obtain information about the frequency content of that specific part of the image. The complete definition is stated below (See Jian-Jiun, 2007).

$$G_x(t,f)=\int_{-\infty}^{\infty}e^{-\pi(\tau-t)^2}e^{-j2\pi f\tau}x(\tau)d\tau,$$

and $$G_x(t,f)=\int_2 2e^{-\pi(\tau-t)^2}e^{-j2\pi f\tau}x(\tau)d\tau.$$

The Gabor transform makes it possible to search for a specific thickness and direction of the needle. The thickness is known beforehand. A search algorithm is used that starts with a number of candidate angles between 0 and 180 degrees, say 4 candidates, and afterwards iteratively zooms in on the best match. This algorithm converges quickly, as it doubles the precision after each iteration cycle. In only 7 iterations, the angle of the needle can be estimated with an accuracy of less than 1 degree. See the table below

| Iteration | Precision (degrees) |
|---|---|
| 1 | 45 |
| 2 | 22.5 |
| 3 | 11.25 |
| 4 | 5.63 |
| 5 | 2.81 |
| 6 | 1.40 |
| 7 | 0.70 |

With filtering, the output of the filter may be correlated to the actual needle position. For example, the sum of all pixels of a filter output turns out to be a good criterion for how close the angle of the needle is to the angle at which the filter output gives a maximum response.

For example, a Gabor transform may be carried out on the projection applied in FIG. 9. The result is a two dimensional data set, in the Gabor domain, which may be visualized. Schematically the visualized image looks like FIG. 10a. The Gabor transform can also be combined with other ways to reduce a 3 dimensional data volume to a two dimension data set.

The high intensities of the needle samples accumulate into an ellipsoidal figure with the orientation of the needle in the data cube. This is one of the benefits of the Gabor transform. To determine this orientation we may use image analysis of the Gabor plane. For example, the image can be de-noised and with simple analysis techniques such as thresholding and segmentation techniques, the ellipsoidal figure is identified. Similarly, by finding the direction with the maximum amount of high luminance (intensity) samples, the primary orientation is found. The primary axis of the ellipsoid figure is shown in FIG. 10b.

The third step in the analysis is shown in FIG. 10c. Here the primary axis of orientation of the ellipsoidal figure is used to construct a plane in the three dimensional data set. This plane contains the needle completely, as the orientation was outlined by the Gabor transform.

If desired, the needle can be detected by taking out this plane from the cube. We have then reduced the problem to detecting the needle in that two dimensional plane. For example, in this plane, the Gabor transform can again be applied, or the needle is found directly with other image analysis techniques, because the data in this plane was already processed in earlier steps.

Below an example is described of the Gabor transform on an image data volume. One frame of the image data volume is shown in FIG. 6. The needle in FIG. 6 has an angle of 103.5 degrees. Using this number as an input, the following estimates are made of the angle:

| Iteration | Guess (degrees) | Error (degrees) |
|---|---|---|
| 1 | 112.5 | 9 |
| 2 | 101.25 | 2.25 |
| 3 | 95.63 | 7.87 |
| 4 | 104.06 | 0.56 |
| 5 | 102.66 | 0.84 |
| 6 | 103.36 | 0.14 |
| 7 | 103.71 | 0.21 |

The algorithm calculates all 7 iterations in about 0.7 seconds using Matlab code. Although the algorithm makes one poor guess at the third iteration, it still converges quickly to the true angle. By manually rotating the input figure 180 times by one degree the algorithm is further tested. It turns out that the algorithm converges to an error of less than one degree within 7 iterations for all 180 tested angles.

After the iterations an estimate of the angle of the needle are known. This leaves the exact location of the needle still open for detection. With the orientation angle of the needle known, there are a number of reasonable localization algorithms with which the needle's position and/or the needle plane can be found. For example, a sample needle with the estimated angle could be (virtually) inserted and then correlated to the image data to find the actual needle's position. Another option would be to use a data matching algorithm such as block matching in motion compensated coding, for which many fast algorithms exist. Our results in convergence and measuring the orientation of the needle indicate that the Gabor transform is a much better choice than the Hough transform. Furthermore, fast algorithms exist for the Gabor transform enabling a real-time implementation.

To summarize, we have found that a directional transform compared to a line sensitive transform is less likely to give false positives, i.e. reporting a needle where there is none; faster; and, more robust in the presence of needle reflections.

FIG. 11 shows a physician performing the procedure on an agar phantom. Shown is a physician inserting a needle 540 into tissue 542 with one hand, while the other holds a medical image acquisition head 520 to guide his actions. An image data volume has previously been obtained by sweeping medical image acquisition head 520 over tissue 542. From the image data volume a needle plane is determined.

The medical image acquisition device also detects the current orientation of the acquisition plane in the image data volume. For example, the data obtained in the current acquisition plane can be correlated to the image data volume. The highest correlation corresponds to the location of the acquisition plane.

The image data acquisition head is movable with respect to the body in operational use. For example, the head may be rotated around an axis, e.g. his centerline or any other axis, or translated along a vector. Typically, a slight translation and/or rotation will be sufficient to correct the alignment. The needle-plane determination module may be configured to determine a difference in direction between the needle-plane and the acquisition plane. By indicating the difference to a user of the medical image acquisition apparatus the difference in orientation, the user can correct the positioning of the head. In this way the acquisition plane is aligned with the needle plane better, allowing better life tracking of the insertion of the needle.

Figure 12:
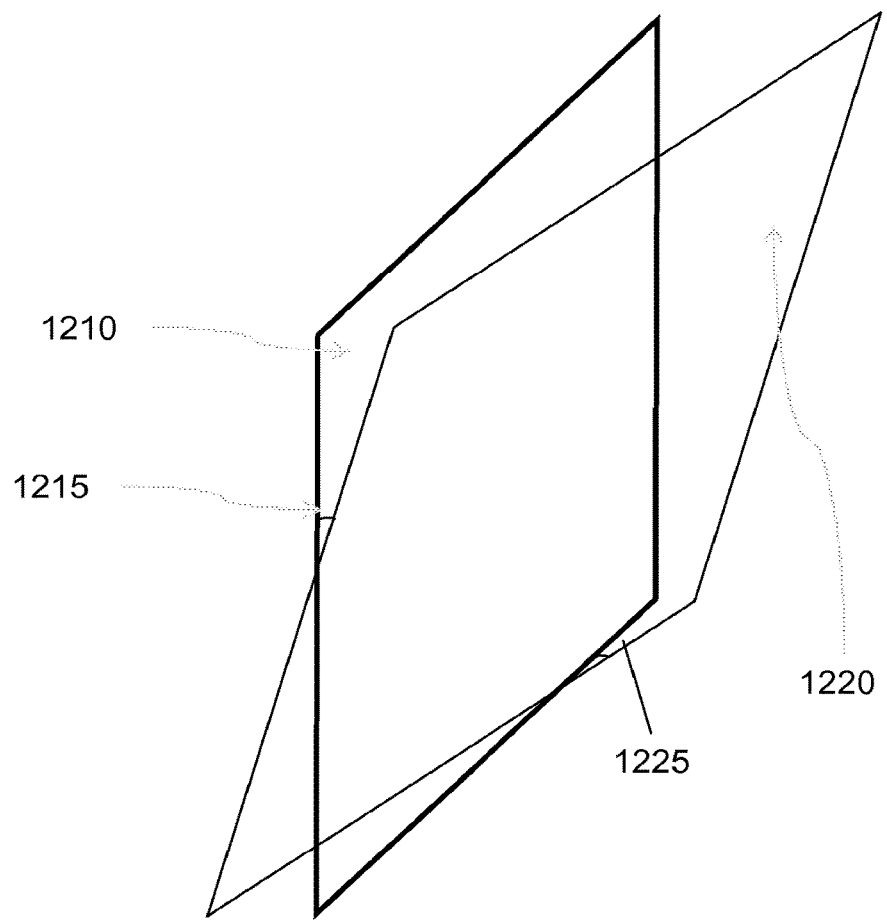
FIG. 12 shows a misalignment between the needle plane and the acquisition plane.

For example, FIG. 12 shows a needle plane 1210 and an acquisition plane 1215 schematically, which are not aligned. By intersecting both planes with a ground plane a difference in orientation can be expressed as an angle; in FIG. 12 as angle 1225. Any projection on a plane allows the measurement of an angle expressing a difference in orientation. For example, by projecting on a plane orthogonal to plane 1210, angle 1215 is obtained. By displaying or otherwise reporting angles 1215 and 1220 to the user, he can correct the orientation of the image acquisition head.

FIG. 4b illustrates with a flow chart a method 440 of visualizing a needle. In step 420 a three dimensional image data volume is obtained of tissue comprising a needle. In step 450 the data volume is projected in the viewing direction onto a projection plane, e.g., a ground plane. In steps 452, 454 and 456 a Gabor transform is applied multiple times for different directions. In step 452 the image data volume projected in step 450 is transformed using the Gabor transform configured for a particular direction. In step 454 the fit of that particular direction is determined. That is, it is determined how well the Gabor transform responds to this image. For example, the total intensity of the transformed image is summed, and taken as a measure of the magnitude of the response of the Gabor transform. In step 456 it is determined if the Gabor transformation must be repeated for further directions. For example, step 456 may control an iteration of a predetermined number of directions, i.e., angles. The directions may be chosen uniformly over 180 degrees. For example, the transform may be repeated 180 times, once for each direction. The direction showing the best fit is kept for later use in the method. A more efficient way, is to partition all directions in a number of sectors, say four quadrants, and perform a Gabor transform for each sector. The sector showing the best fit is iteratively subdivided into smaller sectors for which the process is repeated. In this way the algorithm zooms into the direction with the best fit. In step 458 the projected needle or only the projected needle line is determined. This may be accomplished by correlating the projected image will a number of needle and/or needle lines having the kept direction. The highest found correlation corresponds to the location of the needle. In step 460 the needle plane is determined, as the plane through the needle and/or needle line and parallel to the projecting direction. The algorithm may proceed with locating the precise location of the needle in the needle plane, but this is not necessary. In step 430 the results are visualized, e.g., by showing the intersection of the image data volume with the needle plane.

Note that the method may also be used to determine the needle location without using a viewing direction. In this case the projection may be done in any suitable direction. The projection may be done for different directions if the results are not sufficient, e.g., the projection may be done for three orthogonal directions.

Methods for processing an image data volume acquired from a body comprising a needle with a medical imaging acquisition device can be implemented in various ways. For example, the method may comprise storing a predetermined viewing direction, determining a needle-plane being a plane parallel to and intersecting a representation in the image data volume of the needle and parallel to the viewing direction. The method may work with without a viewing direction in this case the needle-plane need not be parallel to the viewing direction. The method may also determine the location of the needle and/or needle line.

Many different ways of executing the method are possible, as will be apparent to a person skilled in the art. For example, the order of the steps can be varied or some steps may be executed in parallel. Moreover, in between steps other method steps may be inserted either. The inserted steps may represents refinements of the method such as described herein, or may be unrelated to the method. A given step may not have finished completely before a next step is started.

A method according to the invention may be executed using software, which comprises instructions for causing a processor system to perform the method. Software may only include steps taken by a content receiving device, or only those taken by an on-demand server, or only those taken by a broadcaster. The software may be stored in a suitable storage medium, such as a hard disk, a floppy, a memory, etc. The software may be sent as a signal along a wire, or wireless, or using a data network, e.g., the Internet. The software may be made available for download and/or for remote usage on a server.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example, processor instructions and/or interpreter instructions (e.g. Java interpreter instructions). Alternatively, one or more or all of the subroutines may be stored in at least one external library file and linked with a main program either statically or dynamically, e.g. at runtime. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Furthermore, the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

Some of the embodiments according to the invention make use of projection of data. Some of the projection techniques which may be used to implement the invention are summarized below. The embodiment can be combined with different ways of acquiring image data. Different image data acquiring methods are described below.

Projection

In general, projections transform a n-dimensional vector space into a m-dimensional vector space where m<n. Projection of a 3D object onto a 2D surface is done by selecting first the projection surface and then defining projectors or lines which are passed through each vertex of the object. The projected vertices are placed where the projectors intersect the projection surface. The most common (and simplest) projections used for viewing 3D scenes use planes for the projection surface and straight lines for projectors. These are called planar geometric projections.

Figure 8:
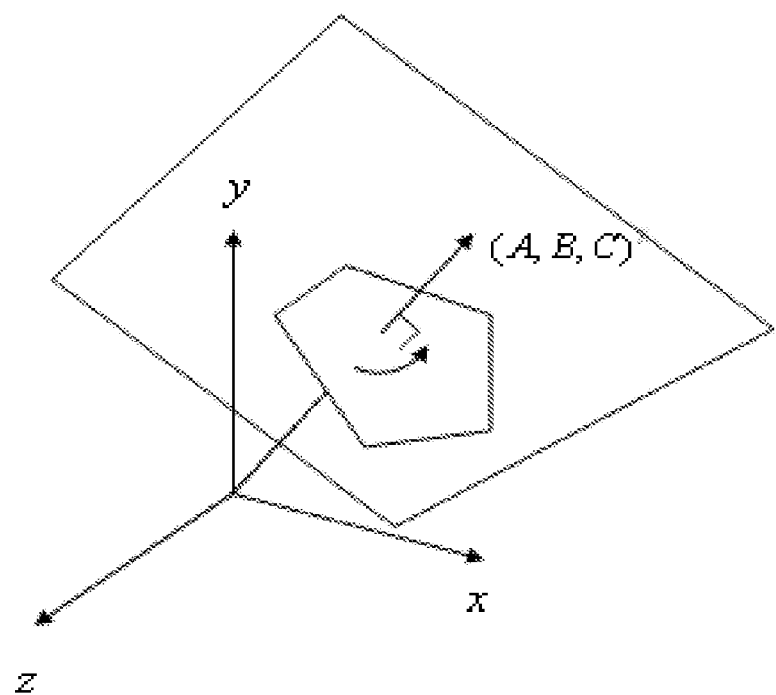
FIG. 8 illustrates the projection plane defined by (ax+by+cz+d=0)

The simplest form of viewing an object is by drawing all its projected edges. In parallel projection (see FIG. 8), we imagine that the eye of the observer is at infinity, and the observer views the scene along a fixed direction vector <a, b, c>. This time, each point (x0, y0, z0) of the scene is projected to the point where the line through (x0, y0, z0) with direction vector <a, b, c> meets a given plane π (a plane with normal vector <a, b, c>.

In parallel projection, the points on an object are projected to the view plane along parallel lines (projectors). The view plane (projection plane) ax+by+cz+d=0 (whose normal $\underline{n}$=<a, b, c>), is intersected with the projector drawn from the object point along a fixed vector $\underline{V}$=<p, q, r>. All the points on the object are projected to the view plane along parallel lines. The views formed by parallel projections vary according to the angle that the directions of projection make with the projection plane and it is classified in to subtypes. If the projection lines are perpendicular (normal) to the image plane of projection, $\underline{V}$ is along the same direction as normal $\underline{n}$ of view plane, then that projection is called the orthographic projection, with <p, q, r>=<a, b, c>. The projection is oblique when the projection is not perpendicular to the image plane of projection, hence <p, q, r>=/=<a,b,c>.

Let ax+by+cz+d=0 be the projection plane, <p, q, r> the direction of the projection and coordinates (x0, y0, z0) be a point on the object to be projected. We start at (x0, y0, z0) and travel along the line in direction <p, q, r> until plane ax+by+cz+d=0 is hit.

The parametric equations of the line are:

$$x=x_0+pt$$

$$y=y_0+qt$$

$$z=z_0+rt$$

At the some value of parameter t, when the plane equation is satisfied, we are on the projection plane, so that $$ax+by+cz+d=0$$

$$a(x_0+pt)+b(y_0+qt)+c(z_0+rt)+d=0$$

$$a+b+c+t(ap+bq+cr)+d=0$$

Solving for the unknown parameter value t, gives $$t = -\left[\frac{ax_0 + by_0 + cz_0 + d}{ap + bq + cr}\right]$$

provided ap+bq+cr=/=0

Substituting this value of t into the previous line equation for x, y and z gives an expression for the projection point (xp, yp, zp):

$$x_p = x_0 - p\left[\frac{ax_0 + by_0 + cz_0 + d}{ap + bq + cr}\right]$$

$$y_p = y_0 - q\left[\frac{ax_0 + by_0 + cz_0 + d}{ap + bq + cr}\right]$$

$$z_p = z_0 - r\left[\frac{ax_0 + by_0 + cz_0 + d}{ap + bq + cr}\right]$$

With some manipulation, we can write this as a matrix equation:

$$[x_p \quad y_p \quad z_p \quad 1] = [x_0 \quad y_0 \quad z_0 \quad 1]\begin{bmatrix} m_{11} & m_{12} & m_{13} & 0 \\ m_{21} & m_{22} & m_{23} & 0 \\ m_{31} & m_{32} & m_{33} & 0 \\ m_{41} & m_{42} & m_{43} & 1 \end{bmatrix}$$

$m_{11} = (bq+cr)/(ap+bq+cr)$   $m_{11} = (bq+cr)/(ap+bq+cr)$
$m_{12} = (-ap)/(ap+bq+cr)$   $m_{12} = (-ap)/(ap+bq+cr)$
$m_{13} = (-ar)/(ap+bq+cr)$   $m_{13} = (-ar)/(ap+bq+cr)$ $m_{11} = (bq+cr)/(ap+bq+cr)$   $m_{11} = (bq+cr)/(ap+bq+cr)$
$m_{12} = (-ap)/(ap+bq+cr)$   $m_{12} = (-ap)/(ap+bq+cr)$
$m_{13} = (-ar)/(ap+bq+cr)$   $m_{13} = (-ar)/(ap+bq+cr)$

Our projector <p, q, r> have same direction as normal vector <a, b, c>. The matrix for projections onto the plane will be:

$$\frac{1}{(a^2+b^2+c^2)}\begin{bmatrix} b^2+c^2 & -ba & -ca & 0 \\ -ab & a^2+c^2 & -cb & 0 \\ -ac & -bc & a^2+b^2 & 0 \\ -ad & -bd & -cd & 1 \end{bmatrix}$$

For the needle detection, we can use this projection matrix to project the 3D dataset onto the 2D surface.

Image Data Acquiring

There are a number of ways to obtain a 3D dataset, which are discussed briefly in this section.

When using ultrasound, typically, the data is captured in intensity images since ultrasound does not involve other components than sound waves. The image data are thus processed in luminance (Y) pictures. If another principle than ultrasound were to be used, the invention may be applied to color images equally well.

A first way to obtain the information along the third dimension is to use a 3D probe. This probe can obtain a dataset in very short time span. If the data to be measured changes over time (i.e. a patient contracts his heart), then this is the preferred way to obtain a good dataset.

The second method to acquire 3D information is to use a regular 2D probe and make successive scans at a fixed interval, as discussed earlier. If time is not a variable and it is possible to make scans at precise intervals, this method is a good way to generate a batch of slices which can be accumulated into a 3D dataset. The data set can be compressed if required, because of its size. This method is, for example, applicable when using a tissue phantom for training purposes. The measured data, and detected needle plane provide good feedback to a physician who is training, e.g. on tissue phantoms, to improve his alignment of an image acquisition head with a needle.

The third method is carefully sliding a 2D probe over the volume of interest maintaining a constant speed while recording the output images in a movie. The slices are afterwards extracted from the resulting movie. This method works well if the scanned volume is sufficiently stable over the time needed to make the sweep, the probe is not tilted while sweeping and the surface is reasonably flat. The advantage over the previous method is that it can be applied to a real patient. The acquired data may be somewhat less accurate than the other methods since a patient always moves a bit and the sweeping speed is never perfectly constant.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

What is claimed is:

1. An ultrasound imaging system comprising:
   an image acquisition head;
   a processor configured to:
   locate a needle tip by projection transformation onto at least one plane;
   determine a needle line in an ultrasound image data volume;
   determine, based on the needle line, a needle plane in the ultrasound image data volume comprising the needle line;
   determine a difference between the needle plane and an acquisition plane acquired by the image acquisition head; and
   generate an indication for display of the difference between the needle plane and the acquisition plane to a user of the system.

2. The system of claim 1, wherein the projection transformation comprises applying a directional transform to the image data volume to determine the needle plane.

3. The system of claim 2, wherein the directional transform comprises a Gabor transform.

4. The system of claim 3, wherein the Gabor transform is applied in multiple directions.

5. The system of claim 1, wherein the indication comprises a representation of relative positions of the needle plane and the acquisition plane.

6. The system of claim 1, wherein the indicating comprises displaying the difference to the user on a display.

7. The system of claim 6, wherein the indicating comprises displaying an angle representing the difference between the needle plane and the acquisition plane.

8. The system of claim 1, wherein the processor is further configured to respond to movement of the image acquisition head until the acquisition plane is aligned with the needle plane and no difference is determined between the acquisition plane and the needle plane.

9. The system of claim 1, wherein determining the needle plane comprises determining an angle of the needle and performing a localization algorithm to determine the needle plane.

10. The system of claim 1, wherein the image data acquisition head comprises a 2D ultrasound probe or a 3D ultrasound probe.

11. The system of claim 1, wherein the processor is configured to determine the needle plane by selecting a plane in the image data volume that includes the needle and is aligned with a viewing direction stored on the system.

12. The system of claim 11, wherein the viewing direction is orthogonal to a surface of a body in which the needle is inserted.

13. The system of claim 11, wherein the viewing direction comprises a direction in which the user is looking at a body in which the needle is inserted.

14. The system of claim 11, wherein the viewing direction is co-planar with the acquisition plane.

15. The system of claim 14, wherein the viewing direction is along a centerline of the acquisition plane.

16. The system of claim 1, wherein the processor is further configured to display the needle plane in relation to the image data volume.

17. The system of claim 15, wherein the viewing direction is predetermined.

18. The system of claim 1, wherein the processor is configured to determine the needle plane using image processing.

* * * * *